(12) United States Patent
Miyamoto et al.

(10) Patent No.: US 12,053,254 B2
(45) Date of Patent: Aug. 6, 2024

(54) INFORMATION PROCESSING APPARATUS AND INFORMATION PROCESSING METHOD

(71) Applicant: SONY CORPORATION, Tokyo (JP)

(72) Inventors: Atsushi Miyamoto, Tokyo (JP); Naoki Kusashima, Tokyo (JP); Ryota Kimura, Tokyo (JP); Kazuo Hongo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 767 days.

(21) Appl. No.: 17/250,397

(22) PCT Filed: Jun. 4, 2019

(86) PCT No.: PCT/JP2019/022227
§ 371 (c)(1),
(2) Date: Jan. 15, 2021

(87) PCT Pub. No.: WO2020/021870
PCT Pub. Date: Jan. 30, 2020

(65) Prior Publication Data
US 2021/0298853 A1 Sep. 30, 2021

(30) Foreign Application Priority Data
Jul. 26, 2018 (JP) ................................ 2018-140669

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/10* (2016.02); *A61B 34/35* (2016.02); *A61B 34/77* (2016.02); *A61B 2034/107* (2016.02)

(58) Field of Classification Search
CPC ... A61B 2034/107; A61B 34/10; A61B 34/35; A61B 34/37; A61B 34/77; A61B 2034/105
(Continued)

(56) References Cited

U.S. PATENT DOCUMENTS

| 5,855,553 | A | 1/1999 | Tajima et al. |
| 7,890,211 | B2 * | 2/2011 | Green ................. H04N 13/337 |
| | | | 901/30 |
| 8,452,372 | B2 * | 5/2013 | Peyman .............. A61F 9/00821 |
| | | | 606/4 |
| 2005/0177096 | A1 | 8/2005 | Bollish |
| 2007/0060874 | A1 | 3/2007 | Nesbitt |

(Continued)

FOREIGN PATENT DOCUMENTS

| CA | 2991711 A1 | 1/2017 |
| CN | 101282693 A | 10/2008 |

(Continued)

OTHER PUBLICATIONS

International Search Report and Written Opinion of PCT Application No. PCT/JP2019/022227, issued on Jul. 16, 2019, 10 pages of ISRWO.

*Primary Examiner* — Chun Cao
(74) *Attorney, Agent, or Firm* — CHIP LAW GROUP

(57) ABSTRACT

There is provided an information processing apparatus that includes a motion request verifying unit controlling execution of a motion request for a device, on the basis of the motion request based on device side information including device state information indicating a state of the device at a first point in time and target state information indicating a state of an operated target, and device side information updated during time after the first point in time and before a second point in time at which the motion request is received.

9 Claims, 14 Drawing Sheets

(51) Int. Cl.
*A61B 34/10* (2016.01)
*A61B 34/35* (2016.01)
(58) Field of Classification Search
USPC .......................................................... 700/3
See application file for complete search history.

(56) References Cited

U.S. PATENT DOCUMENTS

2011/0118748 A1* 5/2011 Itkowitz ................ A61B 90/98
                                                          606/130
2016/0314710 A1   10/2016 Jarc et al.
2018/0200140 A1    7/2018 Ganske et al.
2018/0303667 A1* 10/2018 Peyman ............... A61B 5/0095

FOREIGN PATENT DOCUMENTS

| CN | 101632590 A | 1/2010 |
| CN | 101849849 A | 10/2010 |
| CN | 103702613 A | 4/2014 |
| CN | 106030683 A | 10/2016 |
| CN | 106535812 A | 3/2017 |
| CN | 107361844 A | 11/2017 |
| CN | 107949319 A | 4/2018 |
| CN | 108135658 A | 6/2018 |
| EP | 0732082 A1 | 9/1996 |
| EP | 1125557 A1 | 8/2001 |
| JP | 07-84640 A | 3/1995 |
| JP | 2008-215211 A | 9/2008 |
| JP | 2013236757 A | 11/2013 |
| JP | 2017-510826 A | 4/2017 |
| JP | 2018-521761 A | 8/2018 |
| KR | 20120098342 A | 9/2012 |
| KR | 10-2016-0102464 A | 8/2016 |
| KR | 10-2018-0030601 A | 3/2018 |
| WO | 2015/095715 A1 | 6/2015 |
| WO | 2017/008021 A1 | 1/2017 |
| WO | WO-2017020081 A1 | 2/2017 |

* cited by examiner

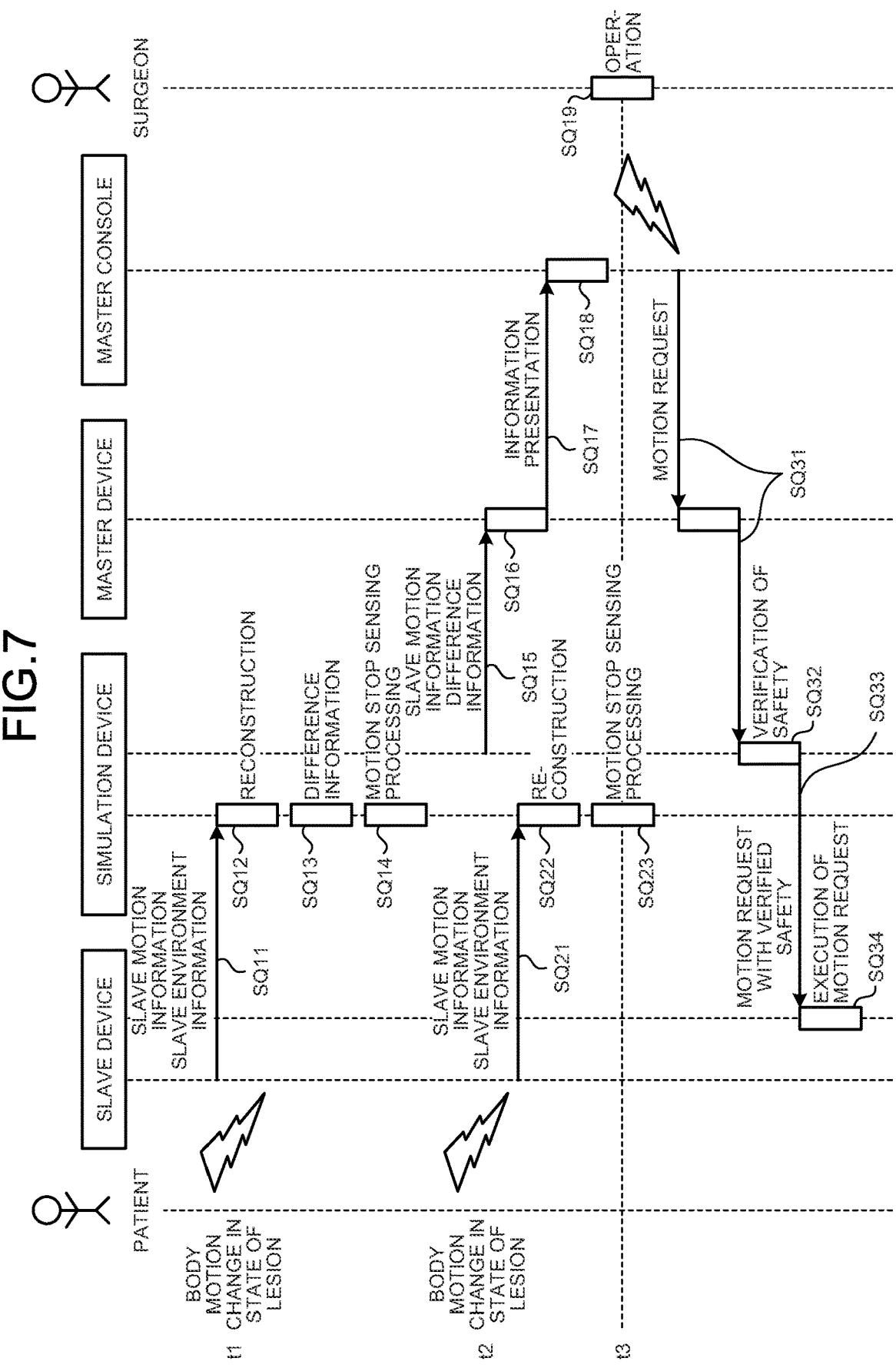

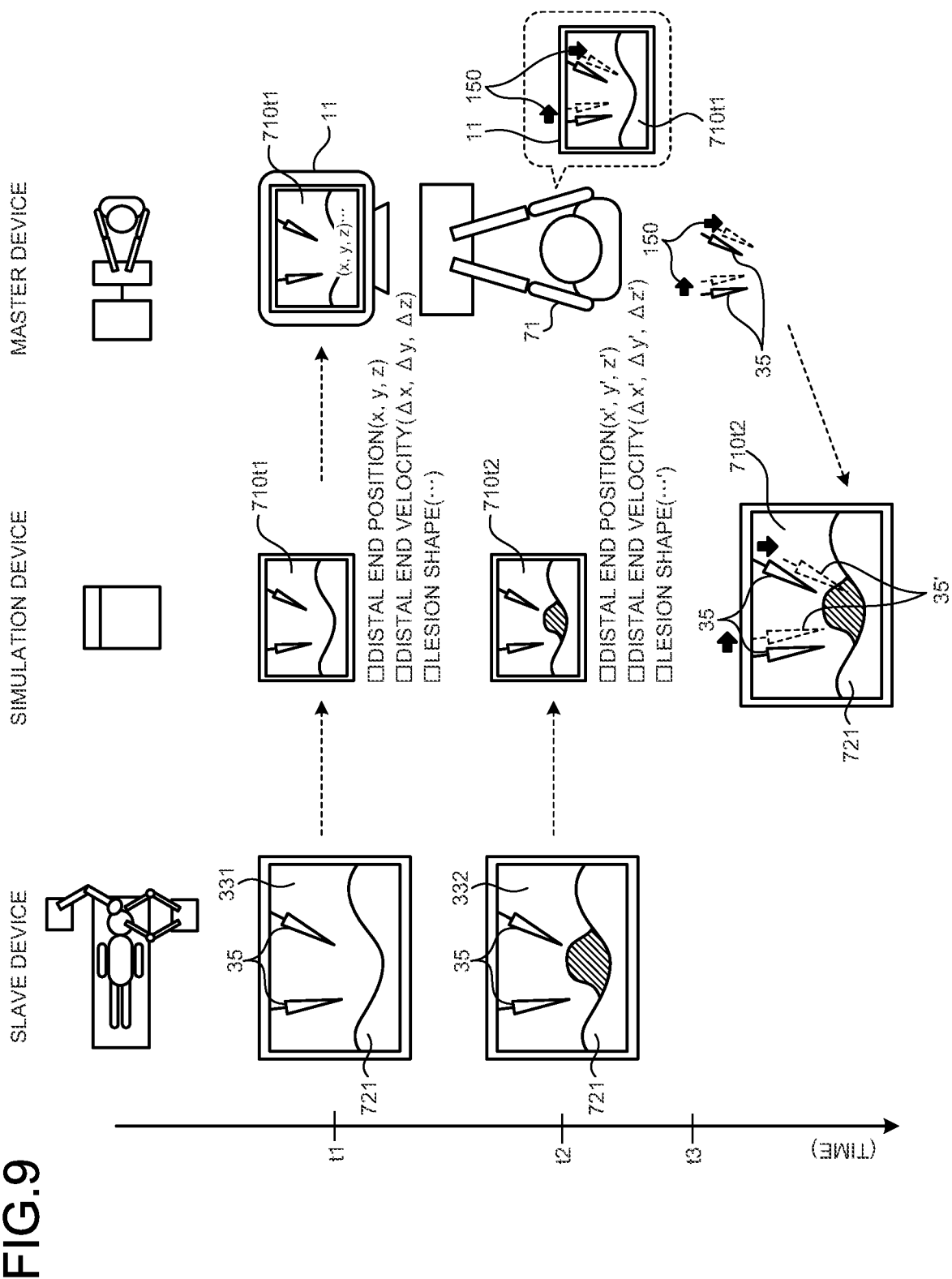

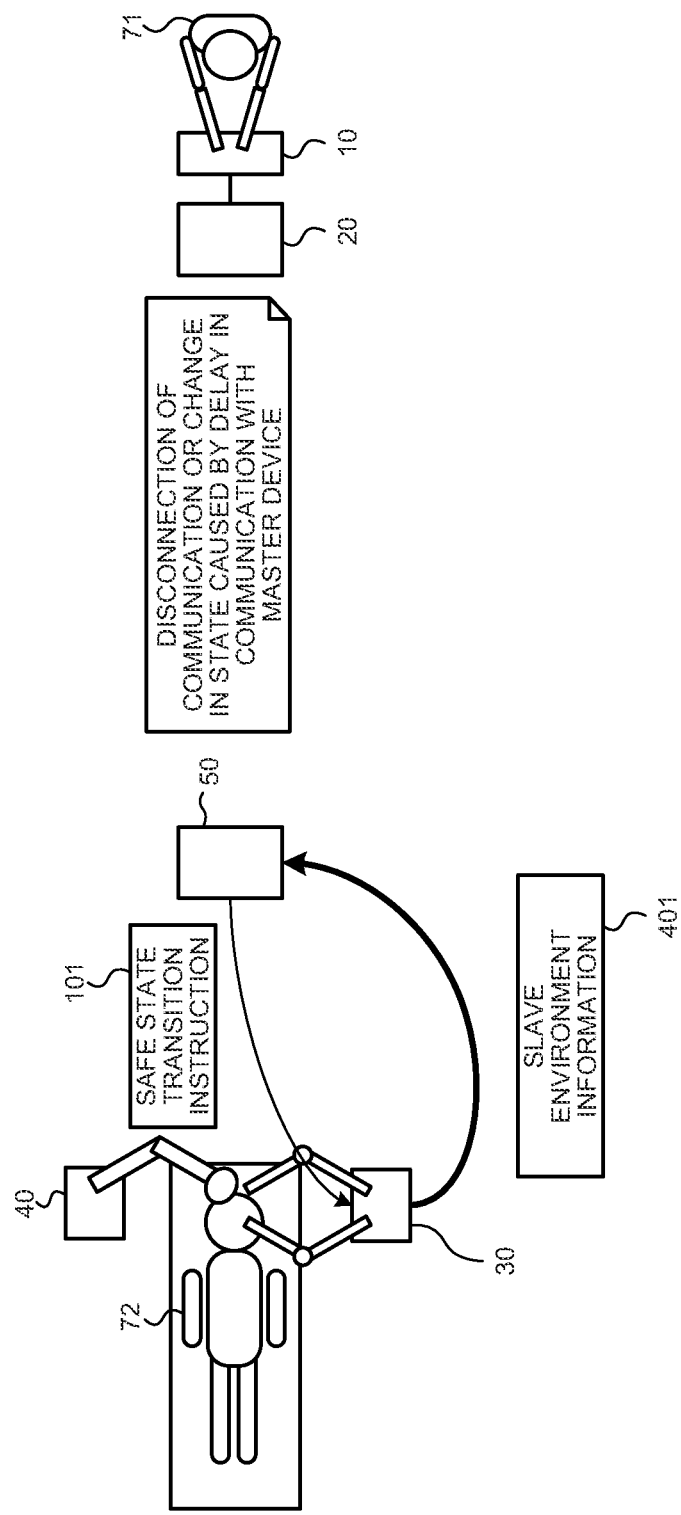

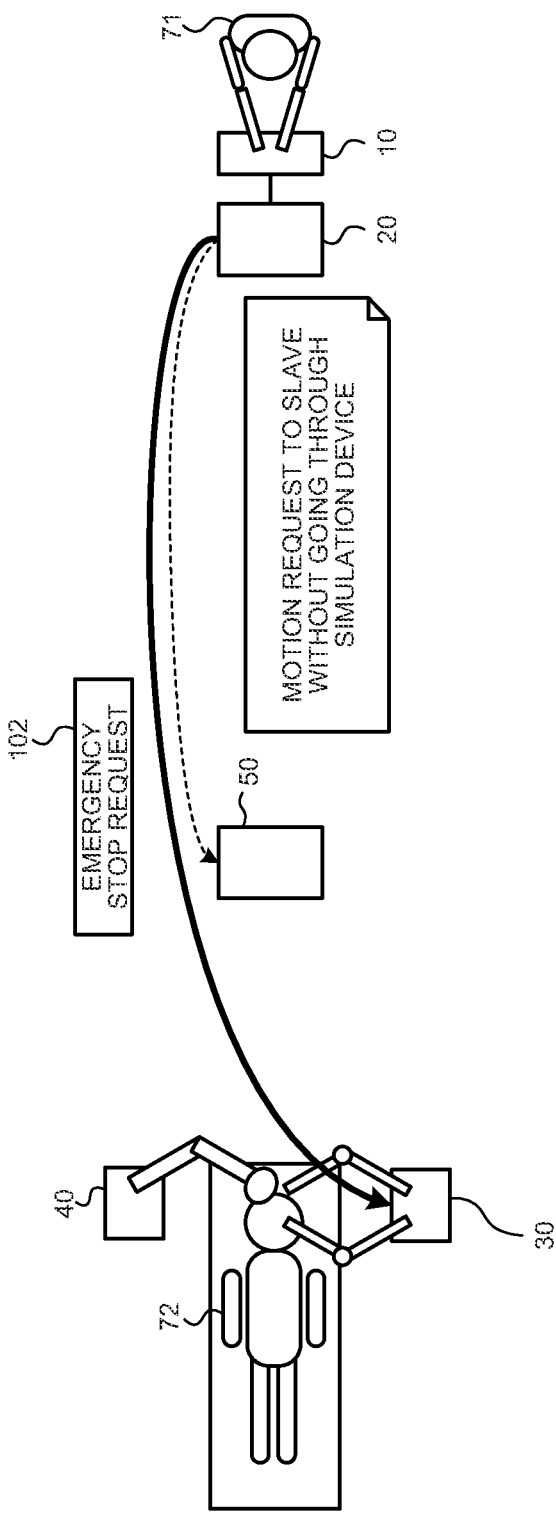

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/022227 filed on Jun. 4, 2019, which claims priority benefit of Japanese Patent Application No. JP 2018-140669 filed in the Japan Patent Office on Jul. 26, 2018. Each of the above-referenced applications is hereby incorporated herein by reference in its entirety.

FIELD

The present disclosure relates to an information processing apparatus, an information processing method, and a computer program.

BACKGROUND

In systems controlling a slave device existing in a remote area by a master-slave control method, a technique of interposing a simulation device simulating motions of the slave device has been proposed.

CITATION LIST

Patent Literature

Patent Literature 1: Japanese Translation of PCT International Application Publication No. 2017-510826
Patent Literature 2: Japanese Patent Application Laid-open No. H7-84640

SUMMARY

Technical Problem

In the conventional art described above, a virtual environment for the slave device is generated with the simulation device and presented to the master device side. For this reason, this structure has a problem in that no safety is considered for a result of executing a motion request for a slave device existing in a remote area.

For this reason, the present disclosure proposes an information processing apparatus, an information processing method, and a computer program capable of verifying safety of a motion of a device serving as an operation target in the case where the device serving as the operation target can be controlled via the information processing apparatus by a master-slave control method.

Solution to Problem

According to the present disclosure, an information processing apparatus is provided that includes: a motion request verifying unit controlling execution of a motion request for a device on the basis of the motion request based on device side information including device state information indicating a state of the device at a first point in time and target state information indicating a state of an operated target, and device side information updated during time after the first point in time and before a second point in time at which the motion request is received.

Advantageous Effects of Invention

The present disclosure enables safety of a motion of the device serving as the operation target in the case where the device serving as the operation target can be controlled via the information processing apparatus by the master-slave control method. The effects described herein are not always limited, but may be any of the effects disclosed in the present disclosure.

BRIEF DESCRIPTION OF DRAWINGS

FIG. 7 is a sequence diagram illustrating an example of a procedure of the information processing method in the remote operation system according to the embodiment.
FIG. 9 is a diagram illustrating details of motion request verification processing in the simulation device.
FIG. 10B is a diagram schematically illustrating an example of flow of information in the remote operation system according to the embodiment.
FIG. 10C is a diagram schematically illustrating an example of flow of information in the remote operation system according to the embodiment.

DESCRIPTION OF EMBODIMENTS

Figure 1:
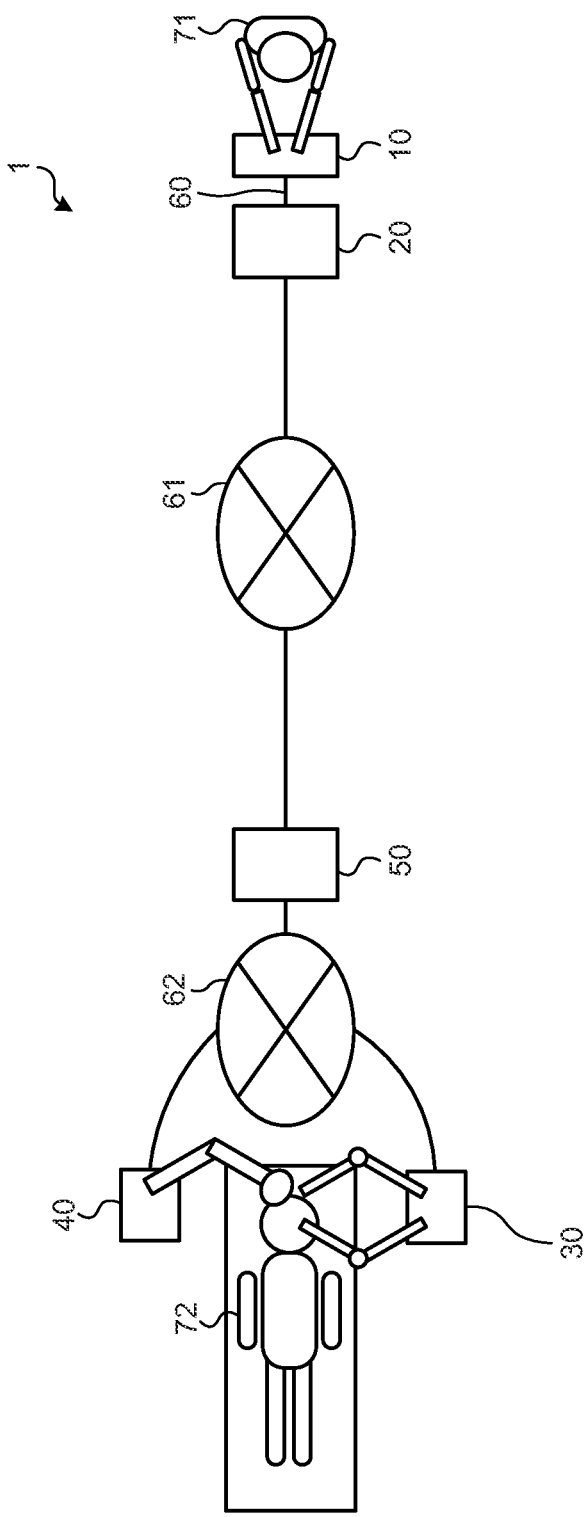
FIG. 1 is a diagram illustrating an example of a schematic configuration of a remote operation system to which an information processing apparatus according to an embodiment of the present disclosure is applied.

An embodiment of the present disclosure will now be described in detail hereinafter with reference to the drawings. In the following embodiment, the same elements are denoted by the same respective reference numerals, and an overlapping explanation thereof is omitted.

Configuration of System According to Embodiment

FIG. 1 is a diagram illustrating an example of a schematic configuration of a remote operation system to which an information processing apparatus according to an embodiment of the present disclosure is applied. The following explanation illustrates a remote medical system in which a surgeon 71 serving as an operator executes treatment for a patient 72 serving as a treatment target by a remote operation, as an example of a remote operation system 1.

The remote operation system 1 includes a master console 10, a master device 20, a slave device 30, a slave environment observation device 40, and a simulation device 50. The master console 10 and the master device 20 are connected via, for example, a communication line 60. The master device 20 and the simulation device 50 are connected via a first network 61. The slave device 30, the slave environment observation device 40, and the simulation device 50 are connected via a second network 62. The master device 20 and the master console 10 are installed in a remote area with respect to the slave device 30, the slave environment observation device 40, and the simulation device 50. For example, the master device 20 and the master console 10 are installed in a building different from a building in which the slave device 30, the slave environment observation device 40, and the simulation device 50 are installed.

A stable network having a smaller delay in communications than that of the first network 61 is used as the second network 62. For example, the second network 62 is a network with shorter update cycles than that of the first network 61. The first network 61 is, for example, a local area network (LAN) including Ethernet (registered trademark), a wide area network (WAN), or the Internet. The second network 62 is a real-time network used in a factory automation (FA) network, or a 5th Generation (5G) wireless communication network or the like. This structure achieves communications with short update cycles and low delay between the simulation device 50, the slave device 30, and the slave environment observation device 40.

The master console 10 is an input/output device connected with the master device 20 and achieving a user interface function for the surgeon 71 executing a surgical operation. The master console 10 includes, for example, a display device, such as a stereoscopic display for the surgeon 71 to recognize the slave environment and an indicator to present information, and an input device, such as a haptic device, a foot pedal, and an emergency stop button. A virtual slave environment serving as a virtual target environment of the lesion of the patient 72 undergoing the surgical operation is presented to the surgeon 71, and the surgeon 71 issues a subsequent motion request on the basis of the presented information.

The master device 20 is a device causing the master console 10 to cooperate with the remote simulation device 50 and the slave device 30. The master device 20 reconstructs the virtual slave environment on the basis of information from the simulation device 50, and transmits a motion request input from the master console 10 for the slave device 30 to the simulation device 50 or the slave device 30. The master device 20 directly transmits a predetermined motion request, such as an emergency stop, to the slave device 30, and transmits the other motion requests to the simulation device 50.

The slave device 30 is a device including a motion execution unit executing treatment for the patient 72 in accordance with the motion request from the master device 20 or the simulation device 50. The motion execution unit is a driven machine, such as a stage and an arm. A distal end of the arm is provided with a gripper for operation and/or a tool for laser irradiation. A plurality of motion execution units may be provided for different uses. The slave device 30 also observes slave motion information serving as a state of the motion execution unit with a sensing unit (sensor), and transmits the slave motion information to the simulation device 50. The slave motion information is a type of device state information.

The slave environment observation device 40 observes slave environment information serving as a state of the patient 72 or a state of the lesion of the patient 72, and transmits the slave environment information to the simulation device 50. The slave environment observation device 40 may be installed independent of the slave device 30, or may be attached to the slave device 30. Examples of the slave environment observation device 40 as described above include a camera imaging the patient 72, in particular, imaging the operative field, a microscope imaging a minute position of the patient 72, and a biological information measurement unit measuring biological information of the patient 72. The biological information is, for example, the blood pressure, the heart rate, and/or the blood flow. Examples of the slave environment observation device 40 attached to the slave device 30 include a tactile sensor and a force sensor at the distal end of the tool of the slave device 30. The slave environment information is a type of target state information indicating a state of the target to be operated. Device side information is information including the device state information and the target state information.

A system between the master device 20 and the slave device 30 may be a unilateral control system or a bilateral control system. In the case of a bilateral control system, with a certain structure of the slave environment observation device 40, the force sense and the tactile sense in the case where the treatment target is operated with the motion execution unit are presented to the surgeon 71 through the haptic device in the input device of the master console 10.

The simulation device 50 generates a virtual slave environment for the treatment target by simulation using the device side information including the slave motion information from the slave device 30 and the slave environment information from the slave environment observation device 40. The virtual slave environment includes the state change of the operative field and the position of the slave device 30. Using the generated virtual slave information, the simulation device 50 determines whether to stop the motion of the slave device 30 at the point in time when the virtual slave information is generated. When the motion of the slave device 30 should be stopped, the simulation device 50 controls the slave device 30 so that the patient 72 is brought into a safe state. In addition, when the simulation device 50 receives a motion request from the master device 20, the simulation device 50 executes simulation of the motion request using the latest virtual slave environment at the point in time, and transmits the motion request to the slave device 30 after safety for the patient 72 is verified. When no safety is verified, the simulation device 50 controls the slave device 30 so that the patient 72 is brought into a safe state. In addition, the simulation device 50 generates difference information from the previously generated virtual slave information for the generated virtual slave environment, and transmits the difference information and the slave motion information to the master device 20. This structure reduces data transmitted from the simulation device 50 to the master device 20, reduces communication delay in the first network 61, and increases the communication cycles.

As described above, to simulate the virtual slave environment without time delay, the simulation device 50 is preferably equipped with a central processing unit (CPU)/graphics processing unit (GPU) having very high arithmetic motion performance. In addition, as described above, because the simulation device 50 is connected with the master device 20 through the first network 61 and connected with the slave device 30 through the second network 62, the simulation device 50 achieves communication with the slave device 30 with lower delay than the master device 20, and achieves stable connection. The simulation device 50 may be installed adjacent to the slave device 30, or may be installed in a server room or an edge cloud as long as the condition described above is satisfied.

Figure 2:
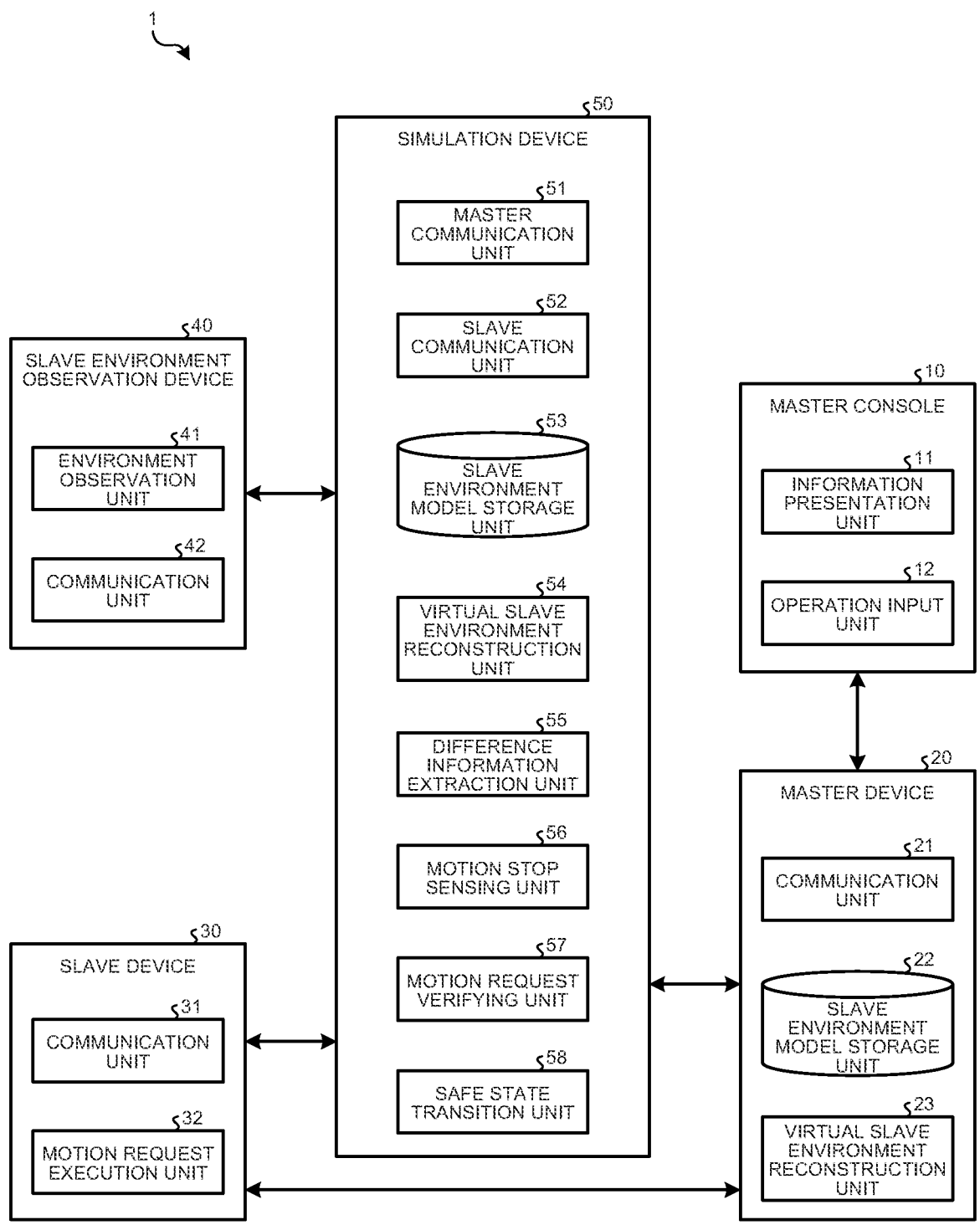
FIG. 2 is a block diagram schematically illustrating a functional configuration of the remote operation system according to the embodiment of the present disclosure.

The following is a detailed explanation of functions of the devices forming the remote operation system 1. FIG. 2 is a block diagram schematically illustrating a functional configuration of the remote operation system according to the embodiment of the present disclosure. The master console 10 includes an information presentation unit 11 and an operation input unit 12.

The information presentation unit 11 is a display device presenting information relating to the operative field of the patient 72 to the surgeon 71. The information relating to the operative field of the patient 72 is, for example, a virtual slave environment reconstructed with the master device 20 or an image obtained by imaging the operative field of the patient 72. The information presentation unit 11 may display both of them simultaneously, or may display one of them. When an image obtained by imaging the operative field with the information presentation unit 11 is displayed, only information of the part imaged with the slave environment observation device 40 is presented. By contrast, when a virtual slave environment is displayed with the information presentation unit 11, because the virtual slave environment is obtained by reconstructing information of the operative field of the patient 72 in a three-dimensional space, the virtual slave information may be displayed at a different angle, or displayed in a closer view. As another example, the information presentation unit 11 may display anatomical information of the patient 72 serving as the target or information relating to the lesion or medical treatment in a state of being overlaid on information relating to the operative field.

The operation input unit 12 is an input device to issue a motion request for the slave device 30 when the patient 72 is treated.

The master device 20 includes a communication unit 21, a slave environment model storage unit 22, and a virtual slave environment reconstruction unit 23. The communication unit 21 performs communications with the simulation device 50 or the slave device 30. The communication unit 21 transmits the input details in the master console 10 to the simulation device 50 or the slave device 30, as a motion request to the slave device 30. When an instruction of emergency stop is input from the master console 10, the communication unit 21 transmits an emergency stop request to the slave device 30. When an instruction other than emergency stop is input from the master console 10, the communication unit 21 transmits the instruction to the simulation device 50, not the slave device 30, as an ordinary motion request.

The slave environment model storage unit 22 stores a slave environment model shared with the simulation device 50, in the case of reconstructing the virtual slave environment with the virtual slave environment reconstruction unit 23. The slave environment model is model information obtained by processing body data of the patient 72 obtained with a three-dimensional tomographic image acquisition device, such as a computed tomography (CT) device.

The virtual slave environment reconstruction unit 23 reconstructs the virtual slave environment using the difference information and the slave motion information transmitted from the simulation device 50 for the slave environment model stored in the slave environment model storage unit 22. In the present specification, suppose that reconstruction of the virtual slave environment includes update using the difference information and the slave motion information. The virtual slave environment reconstructed herein is output to the information presentation unit 11 of the master console 10.

The slave environment observation device 40 includes an environment observation unit 41 and a communication unit 42. The environment observation unit 41 is an observation device observing the slave environment information being a state of the patient 72 serving as the slave environment. The slave environment includes visual information and non-visual information of the patient 72 serving as the target. Examples of the visual information include the state of the appearance of the patient 72 and the state of the lesion, and the like. The environment observation unit 41 acquiring visual information is, for example, a camera imaging the operative field of the patient 72. Examples of the non-visual information include the blood pressure and the heart rate of the patient 72. The environment observation unit 41 acquiring non-visual information is, for example, a sphygmomanometer or a heart rate meter.

The communication unit 42 transmits the slave environment information observed with the environment observation unit 41 to the simulation device 50.

The slave device 30 includes a communication unit 31 and a motion request execution unit 32. The communication unit 31 performs communications with the master device 20 or the simulation device 50. For example, the communication unit 31 receives a motion request including an emergency stop request from the master device 20 or the simulation device 50. The communication unit 31 also acquires the slave motion information being the state of the motion execution unit of the slave device 30 from the sensing unit provided in the motion execution unit, and transmits the slave motion information to the simulation device 50. The slave motion information is the position and the motion state of the motion execution unit. For example, when the motion execution unit is an arm, the slave motion information is an angle of the arm and the distance of the distal end of the arm from the lesion, and the like.

The simulation device 50 includes a master communication unit 51, a slave communication unit 52, a slave environment model storage unit 53, a virtual slave environment reconstruction unit 54, a difference information extraction unit 55, a motion stop sensing unit 56, a motion request verifying unit 57, and a safe state transition unit 58.

The master communication unit 51 performs communications with the master device 20. Specifically, the master communication unit 51 receives a motion request other than the emergency stop request from the master device 20. The master communication unit 51 also transmits the slave motion information and the difference information to the master device 20.

The slave communication unit 52 performs communications with the slave device 30 and the slave environment observation device 40. Specifically, the slave communication unit 52 receives the slave environment information from the slave environment observation device 40 and the slave motion information from the slave device 30. When the safe state transition unit 58 determines that transition to the safe state is required, the slave communication unit 52 transmits a motion switch instruction to the slave device 30. In addition, when safety with respect to the motion request is verified in the motion request verifying unit 57, the slave communication unit 52 transmits a motion request to the slave device 30.

The slave environment model storage unit 22 stores therein a slave environment model shared with the master device 20, when the virtual slave environment is reconstructed with the virtual slave environment reconstruction unit 54.

The virtual slave environment reconstruction unit 54 reconstructs the virtual slave environment using the slave motion information transmitted from the slave device 30 and the slave environment information transmitted from the slave environment observation device 40 for the slave environment model stored in the slave environment model storage unit 22. The virtual slave environment reconstruction unit 54 corresponds to the virtual target environment reconstruction unit.

The difference information extraction unit 55 extracts difference information by which the virtual slave environment changes in time series between the previous time and the current time, and transmits the difference information to the master device 20, when model information is shared in advance between the master device 20 and the simulation device 50. Specifically, the difference information extraction unit 55 extracts, as the difference information, a difference between the first virtual slave environment reconstructed with the virtual slave environment reconstruction unit 54 and the second virtual slave environment reconstructed with the virtual slave environment reconstruction unit 54 before the first virtual slave environment. The difference information is transmitted to the master device 20 via the master communication unit 51.

The motion stop sensing unit 56 senses occurrence of a situation in which the motion of the slave device 30 is to be stopped, when the virtual slave environment is reconstructed with the virtual slave environment reconstruction unit 54. The motion stop sensing unit 56 determines whether the slave device 30 satisfies a motion stop condition indicating the condition to stop the motion of the slave device 30, for example, from the reconstructed virtual slave environment, and notifies the safe state transition unit 58 of a stop condition occurrence notification when the motion stop condition is satisfied. The motion stop sensing unit 56 also notifies the master device 20 of the stop condition occurrence notification via the master communication unit 51.

Examples of the motion stop condition include a state in which the motion execution unit of the slave device 30 does not move in accordance with the motion request, a state in which the motion execution unit of the slave device 30 invades a place other than the lesion of the patient 72, a state in which the part around the lesion deviates from the ordinary state, such as a state in which the part around the lesion is extremely deformed, and a state in which the biological information of the patient 72 exceeds the assumed range. The biological information of the patient 72 is, for example, the heart rate, the blood pressure, the blood oxygenation level, and the hemorrhage.

When the motion request verifying unit 57 receives a motion request from the master device 20, the motion request verifying unit 57 executes simulation of the motion request using the virtual slave environment that has been reconstructed at the point in time when the motion request is received, and verifies the safety of the patient 72. The safety of the patient 72 is verified using the safety determination standard. Examples of the safety determination standard include a state in which the motion execution unit of the slave device 30 moves within the preset range of the position, the velocity, and the acceleration, a state in which the motion execution unit of the slave device 30 contacts the lesion within a preset force range, and a state in which the part around the lesion is not extremely deformed by a motion of the motion execution unit of the slave device 30.

As a result of simulation, when safety of the patient 72 is verified, the motion request verifying unit 57 transmits the motion request from the master device 20 to the slave device 30 through the slave communication unit 52. In addition, when safety of the patient 72 is not verified as a result of simulation, the motion request verifying unit 57 does not transmit the motion request from the master device 20 to the slave device 30, but notifies the safe state transition unit 58 of a stop condition occurrence notification. In addition, the motion request verifying unit 57 notifies the master device 20 of the stop condition occurrence notification via the master communication unit 51.

When the safe state transition unit 58 receives a stop condition occurrence notification from the motion stop sensing unit 56 or the motion request verifying unit 57, the safe state transition unit 58 transmits a motion switch instruction to cause the slave device 30 to execute a motion to secure safety to the slave device 30. The motion switch instruction is an instruction to execute switching to a motion to secure safety of the patient 72 from processing performed in accordance with the motion request transmitted from the master device 20. The contents of the motion switch instruction differ according to the position of the motion execution unit of the slave device 30 with respect to the patient 72. For example, when the motion execution unit is positioned in a place distant from the patient 72, the motion execution unit is stopped in that state. As another example, when the motion execution unit is in contact with the patient 72, the motion execution unit is moved to be separated from the patient 72, and thereafter stopped.

Process According to Embodiment

The following is an explanation of processing executed in the slave environment observation device 40, the slave device 30, the simulation device 50, and the master device 20 forming the remote operation system 1.

Figure 3:
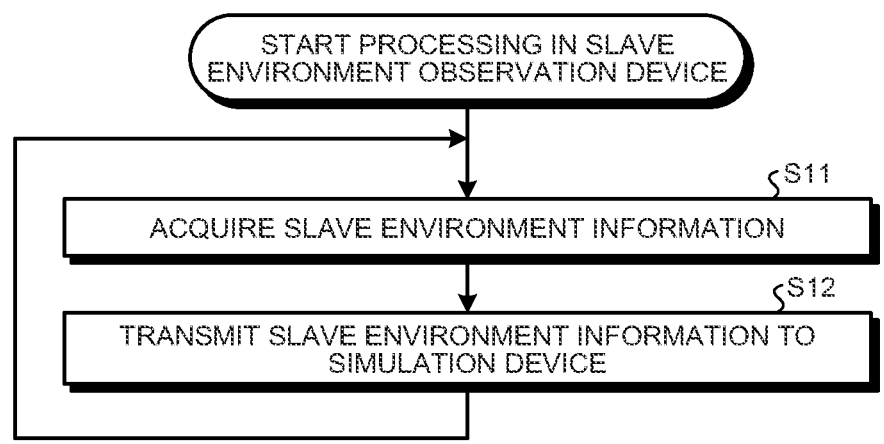
FIG. 3 is a flowchart illustrating an example of a process in a slave environment observation device.

FIG. 3 is a flowchart illustrating an example of a process executed in the slave environment observation device. The environment observation unit 41 of the slave environment observation device 40 acquires slave environment information serving as information for the patient 72 (Step S11). The slave environment information is imaging data of the lesion of the patient 72 and/or biological information of the patient 72, such as the blood pressure and the heart rate, as described above. Thereafter, the communication unit 42 transmits the acquired slave environment information to the simulation device 50 (Step S12). The processing described above is executed while the remote operation system 1 is working.

Figure 4:
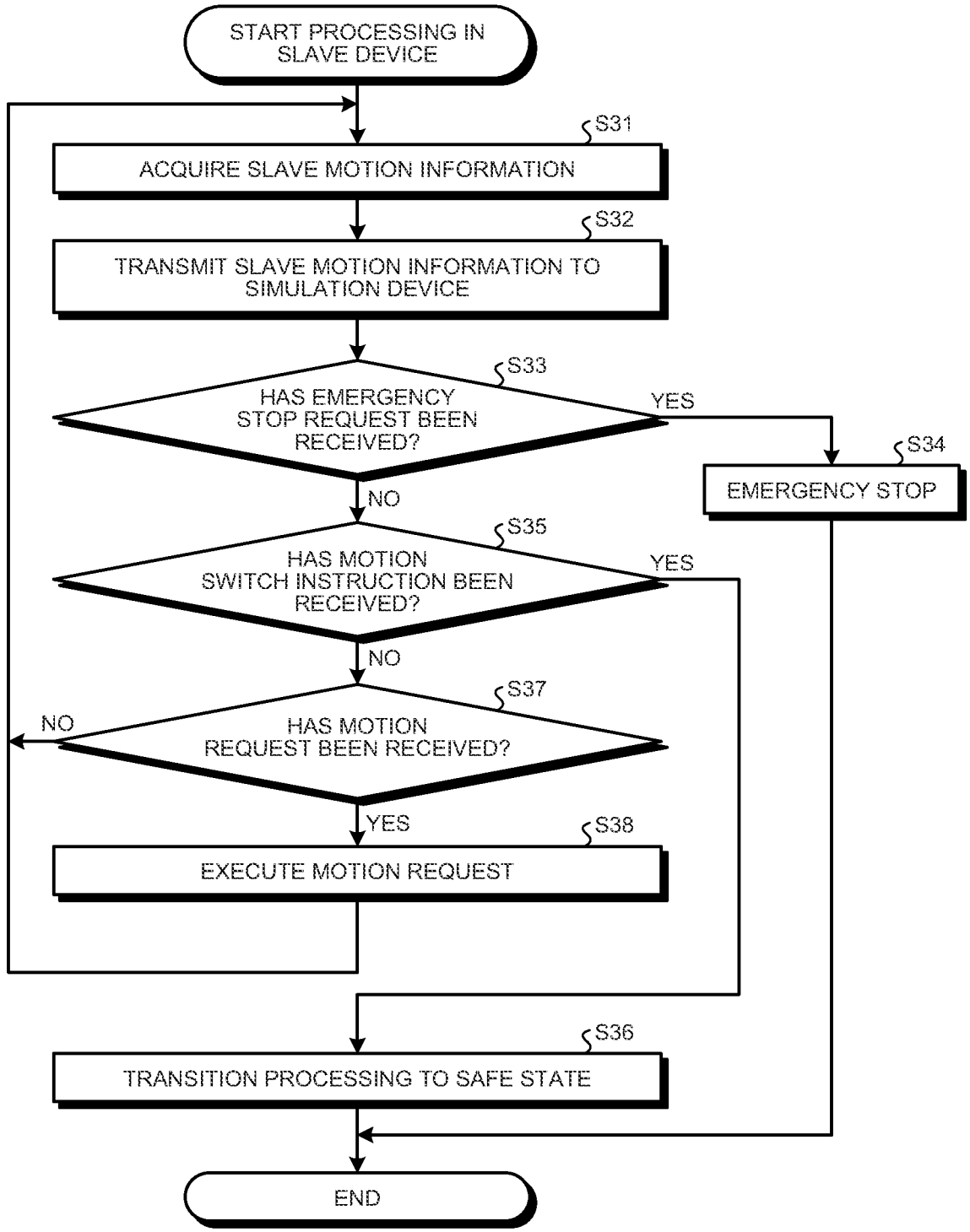
FIG. 4 is a flowchart illustrating an example of a processing procedure in a slave device.

FIG. 4 is a flowchart illustrating an example of a processing procedure in the slave device. First, the communication unit 31 of the slave device 30 acquires slave motion information indicating the motion state for the motion execution unit from the sensing unit included in the motion execution unit (Step S31), and transmits the slave motion information to the simulation device 50 (Step S32).

Thereafter, the motion request execution unit 32 determines whether an emergency stop request has been received from the master device 20 (Step S33). When an emergency stop request has been received (Yes at Step S33), the motion request execution unit 32 executes emergency stop of the motion execution unit (Step S34). In this manner, the slave device 30 stops the motion, and the processing is ended.

By contrast, when no emergency stop request has been received (No at Step S33), the motion request execution unit 32 determines whether a motion switch instruction has been received from the simulation device 50 (Step S35). When a motion switch instruction has been received (Yes at Step S35), the motion request execution unit 32 executes processing of changing the motion of the slave device 30 to the safe state (Step S36). Examples of the processing of changing the motion to the safe state include stop of the motion execution unit of the slave device 30 and withdrawal of the motion execution unit to a position in which the motion execution unit does not contact the patient 72. Thereafter, the processing is ended.

In addition, when no motion switch instruction has been received (No at Step S35), the motion request execution unit 32 determines whether a motion request has been received (Step S37). When a motion request has been received (Yes at Step S37), the motion request execution unit 32 executes the motion request (Step S38). Thereafter or when no motion request has been received at Step S37 (No at Step S37), the processing returns to Step S31.

Figure 5:
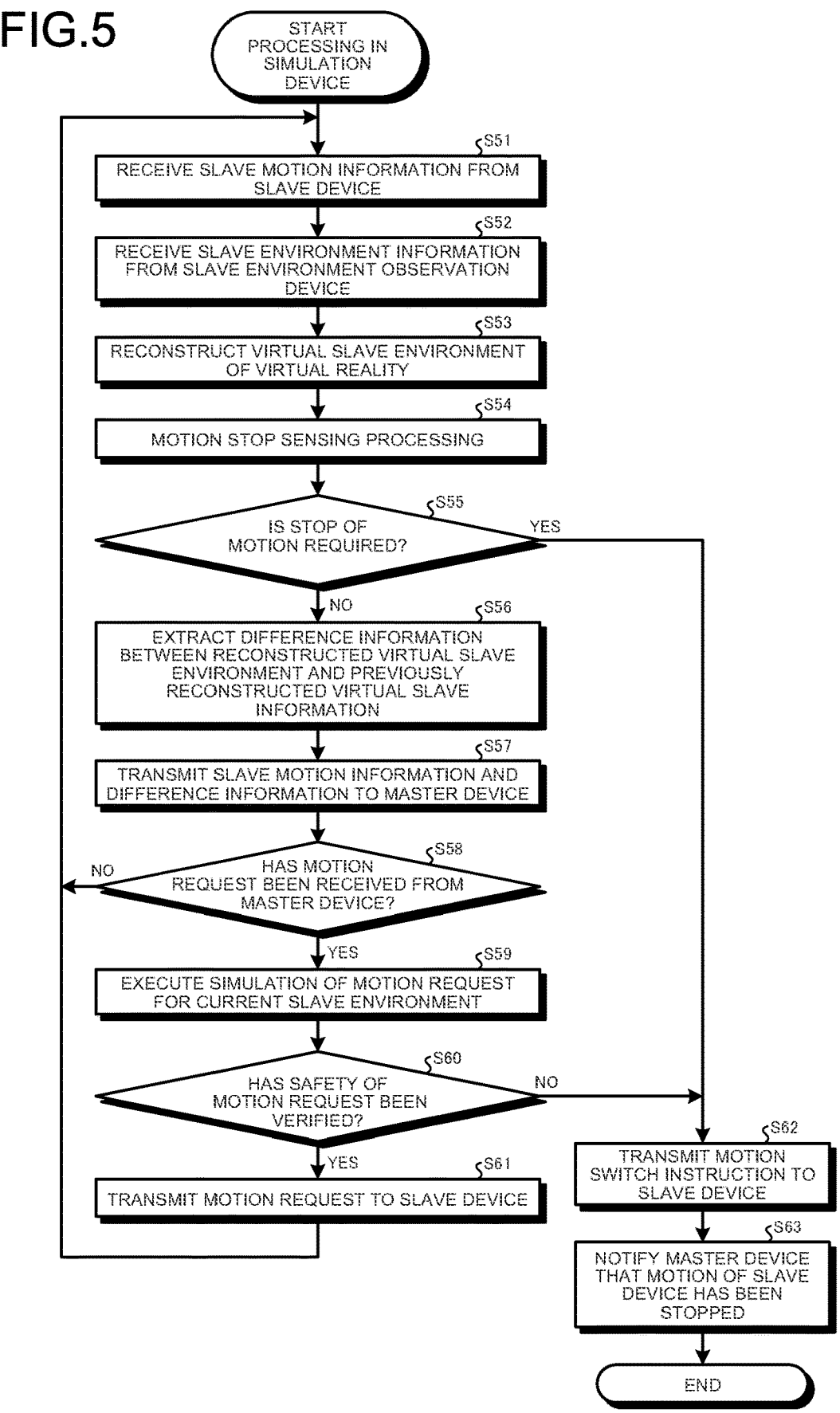
FIG. 5 is a flowchart illustrating an example of a processing procedure of an information processing method in a simulation device.

FIG. 5 is a flowchart illustrating an example of a processing procedure of an information processing method in the simulation device. First, the slave communication unit 52 of the simulation device 50 receives slave motion information from the slave device 30 (Step S51), and receives slave environment information from the slave environment observation device 40 (Step S52). Thereafter, the virtual slave environment reconstruction unit 54 reconstructs the virtual slave environment of virtual reality using device side information including the received slave motion information and the slave environment information (Step S53). In this state, when a slave environment model is stored in the slave environment model storage unit 53, the slave environment model is also used.

Thereafter, using the reconstructed virtual slave environment, the motion stop sensing unit 56 executes motion stop sensing processing of determining whether to stop the motion of the slave device 30 (Step S54). For example, the motion stop sensing unit 56 determines whether to stop the motion of the slave device 30 by determining whether the virtual slave environment satisfies the motion stop condition. As a result, when it is not required to stop the motion of the slave device 30 (No at Step S55), the difference information extraction unit 55 extracts difference information between the reconstructed virtual slave environment and the previously reconstructed virtual slave environment (Step S56). Thereafter, the master communication unit 51 transmits the slave motion information and the difference information to the master device 20 (Step S57).

Thereafter, the master communication unit 51 determines whether a motion request has been received from the master device 20 (Step S58). When a motion request has been received from the master device 20 (Yes at Step S58), the motion request verifying unit 57 executes simulation of the received motion request for the current virtual slave environment, that is, the virtual slave environment reconstructed at Step S53 (Step S59). Thereafter, the motion request verifying unit 57 determines whether safety of the motion request has been verified as a result of the simulation (Step S60). For example, the motion request verifying unit 57 determines safety of the motion request by determining whether the result of the simulation satisfies the safety determination standard.

When safety of the motion request has been verified (Yes at Step S60), the slave communication unit 52 transmits the motion request received from the master device 20 to the slave device 30 (Step S61). Thereafter or when no motion request has been received from the master device 20 at Step S58 (No at Step S58), the processing returns to the step S51.

When safety of the motion request has not been verified (No at Step S60) or when the motion should be stopped at Step S55 (Yes at Step S55), the safe state transition unit 58 transmits a motion switch instruction to the slave device 30 (Step S62). In addition, the safe state transition unit 58 notifies the master device 20 that the motion of the slave device 30 has been stopped (Step S63). Thereafter the processing is ended.

As described above, execution of the motion request is simulated using the latest virtual slave environment at the point in time the motion request is received, and it is controlled whether to transmit the motion request to the slave device 30 on the basis of the result of the simulation. This structure enables interruption of processing without verification by the surgeon 71 being the operator of the master device 20, in the case where the motion request that was safe when the request was instructed at the master console 10 has been changed to one for which safety cannot be verified when the request has been received with the simulation device. This structure enables securement of safety of the patient 72 also in the actual space.

Figure 6:
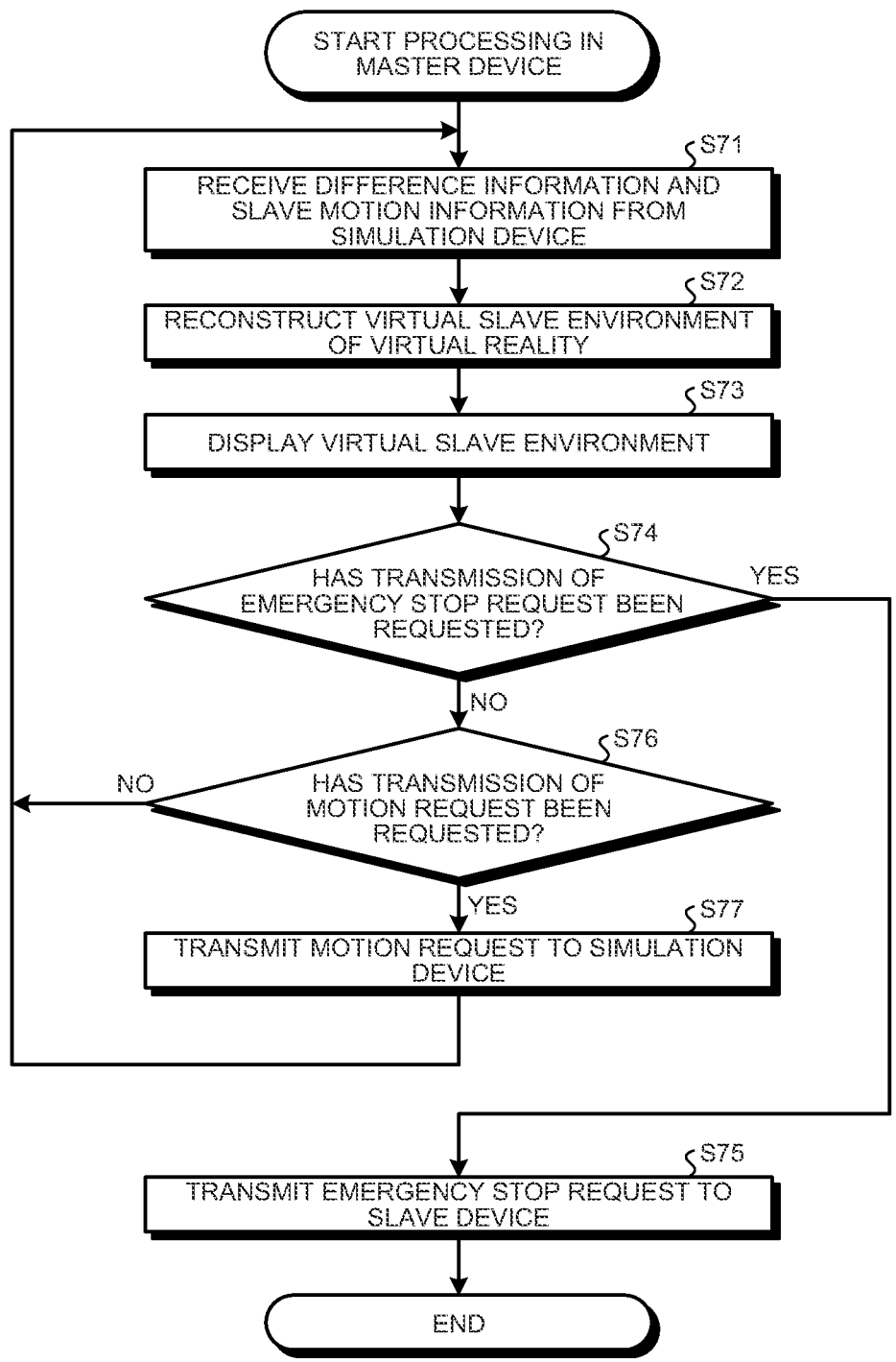
FIG. 6 is a flowchart illustrating an example of a processing procedure in a master device.

FIG. 6 is a flowchart illustrating an example of a processing procedure in the master device. First, the communication unit 21 of the master device 20 receives difference information and slave motion information from the simulation device 50 (Step S71). Thereafter, the virtual slave environment reconstruction unit 23 reconstructs a virtual slave environment of virtual reality using the received slave motion information and the received difference information (Step S72). At this step, when a slave environment model is stored in the slave environment model storage unit 22, the slave environment model is also used.

Thereafter, the information presentation unit 11 of the master console 10 displays the reconstructed virtual slave environment (Step S73). The surgeon 71 being the operator operates the operation input unit 12 while viewing the virtual slave environment displayed on the information presentation unit 11. The communication unit 21 of the master device 20 determines whether transmission of an emergency stop request has been requested from the operation input unit 12 of the master console 10 (Step S74).

When transmission of an emergency stop request has been requested (Yes at Step S74), the communication unit 21 transmits an emergency stop request to the slave device 30 (Step S75), and the processing is ended.

When transmission of an emergency stop request has not been requested (No at Step S74), the communication unit 21 determines whether transmission of a motion request has been requested from the operation input unit 12 of the master console 10 (Step S76). When transmission of a motion request has been requested (Yes at Step S76), the communication unit 21 transmits a motion request to the simulation device 50 (Step S77).

Thereafter or when transmission of a motion request has not been requested (No at Step S76), the processing returns to Step S71.

The following is an explanation of flow of processing between the slave environment observation device 40, the slave device 30, the simulation device 50, the master device 20, and the master console 10 forming the remote operation system 1. FIG. 7 is a sequence diagram illustrating an example of a procedure of the information processing method in the remote operation system according to the embodiment. FIGS. 8A, 8B, 8C, and 8D are diagrams schematically illustrating a positional relation between the lesion of the patient and the motion execution part of the slave device. FIG. 9 is a diagram illustrating details of motion request verification processing in the simulation device.

First, at time t1, the slave environment observation device 40 observes the state of the patient 72, and the slave device 30 observes (acquires) the state of the motion execution unit. For example, the states of a motion execution unit 35 of the slave device 30 and a lesion 721 of the patient 72 illustrated in a slave environment 331 in FIG. 9 are acquired. The shape of the lesion 721 is acquired as the slave environment information, and the distal end position and the velocity and the like of the motion execution unit 35 are acquired as the slave motion information.

Thereafter, the slave device 30 transmits the slave motion information to the simulation device 50 via the second network 62, and the slave environment observation device 40 transmits the slave environment information to the simulation device 50 via the second network 62 (SQ11 in FIG. 7).

Thereafter, the simulation device 50 reconstructs a virtual slave environment 710t1 as illustrated in FIG. 9 using the received slave motion information and the slave environment information (SQ12 in FIG. 7). As described above, when a slave environment model of the patient 72 exists, the virtual slave environment is reconstructed using the slave motion information and the slave environment information on the basis of the slave environment model.

Thereafter, the simulation device 50 extracts difference information serving as a difference between the reconstructed virtual slave environment and the previously reconstructed virtual slave environment (SQ13 in FIG. 7). In this example, the difference information is, for example, a difference between the virtual slave environment 710t1 at the time t1 and a virtual slave environment at time t0 (not illustrated).

Figure 8A:
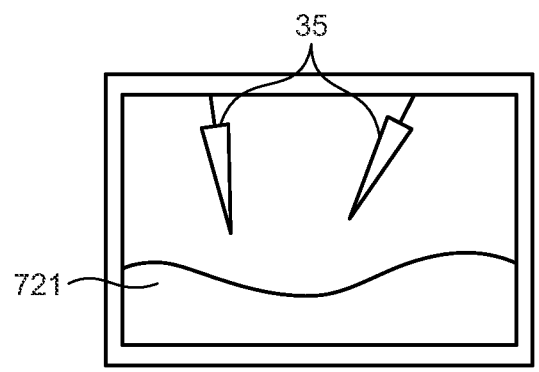
FIG. 8A is a diagram schematically illustrating a positional relation between a lesion of a patient and a motion execution part of the slave device.

In addition, the simulation device 50 executes motion stop sensing processing using the reconstructed virtual slave environment (SQ14 in FIG. 7). FIGS. 8A, 8B, 8C, and 8D illustrate an example of the motion stop sensing processing. For example, FIG. 8A illustrates a state in which the motion execution unit 35 of the slave device 30 exists in a position as requested with the motion request received before, and the lesion 721 of the patient 72 is not invaded with the motion execution unit 35. As described above, when the motion execution unit 35 moves in accordance with the motion request and does not invade a place other than the lesion 721 of the patient 72 and the part around the lesion 721 is not extremely deformed but is in an ordinary state, the condition to stop the motion is not satisfied, and the motion of the slave device 30 is continued without any change.

Figure 8B:
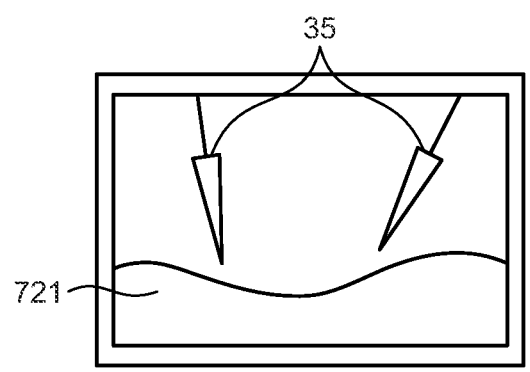
FIG. 8B is a diagram schematically illustrating a positional relation between the lesion of the patient and the motion execution part of the slave device.
Figure 8C:
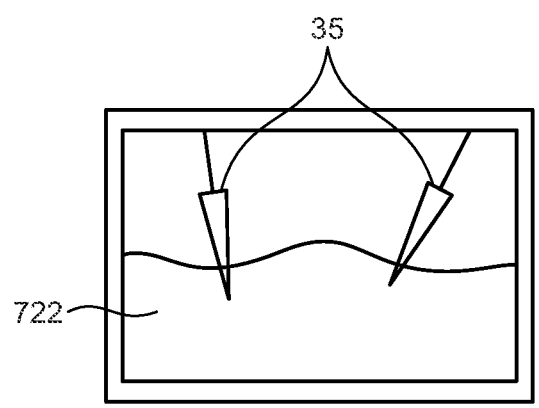
FIG. 8C is a diagram schematically illustrating a positional relation between the lesion of the patient and the motion execution part of the slave device.
Figure 8D:
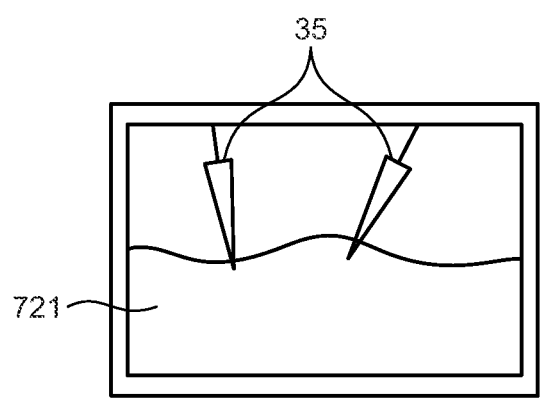
FIG. 8D is a diagram schematically illustrating a positional relation between the lesion of the patient and the motion execution part of the slave device.

FIG. 8B illustrates an example in the case where the motion execution unit 35 of the slave device 30 does not move in accordance with the motion request, and FIG. 8C illustrates an example in the case where the motion execution unit 35 of the slave device 30 does not move in accordance with the motion request and the motion execution unit 35 invades a place 722 other than the lesion 721 of the patient 72. FIG. 8D illustrates an example in the case where the part around the lesion 721 is extremely deformed and deviates from the ordinary state. In the case where the state corresponds to any of the states in FIGS. 8B, 8C, and 8D, the condition to stop the motion is satisfied, and the simulation device 50 changes the slave device 30 to the safe state. In this example, suppose that the slave device 30 does not satisfy the condition to stop the motion, as illustrated in FIG. 8A.

With reference to FIG. 7 again, the simulation device 50 transmits the slave motion information and the difference information to the master device 20 via the first network 61 (SQ15 in FIG. 7). Thereafter, the master device 20 reconstructs the virtual slave environment using the received slave motion information and the received difference information (SQ16 in FIG. 7), and presents the information to the master console 10 (SQ17 in FIG. 7). As illustrated in FIG. 9, the virtual slave environment 710t1 is displayed on the information presentation unit 11 of the master console 10.

The lesion 721 changes every moment, and the motion execution unit 35 of the slave device 30 requires time to change to the motion-requested state. For this reason, the slave device 30 and the slave environment observation device 40 acquire slave motion information and slave environment information at, for example, certain cycles, and transmit the information to the simulation device 50 (SQ21 in FIG. 7). In this example, the states of the motion execution unit 35 of the slave device 30 and the lesion 721 of the patient 72 illustrated in a slave environment 332 at time t2 in FIG. 9 are acquired as the slave environment information and the slave motion information, and transmitted to the simulation device 50.

Thereafter, the simulation device 50 reconstructs a virtual slave environment 710t2 using the slave motion information and the slave environment information at the time t2, as illustrated in FIG. 9 (SQ22 in FIG. 7). The structure is based on the premise that the update cycles of the first network 61 is longer than the update cycles of the second network 62, the virtual slave environment 710t2 is not transmitted to the master device 20. In addition, the simulation device 50 executes motion stop sensing processing using the reconstructed virtual slave environment 710t2 (SQ23 in FIG. 7). Suppose that the slave device 30 does not satisfy the condition to stop the motion also at this step.

By contrast, the surgeon 71 executes an operation at time t3 while viewing the virtual slave environment 710t1 displayed on the master console 10 at SQ17 (SQ18 in FIG. 7). The operation on the operation input unit 12 of the master console 10 by the surgeon 71 is transmitted as a motion request from the master device 20 to the simulation device 50 (SQ31 in FIG. 7). For example, in FIG. 9, when the surgeon 71 operates the operation input unit 12 to move the motion execution unit 35 to a desired position while viewing the virtual slave environment 710t1 displayed on the information presentation unit 11, a motion request 150 is generated.

When the simulation device 50 receives a motion request, the simulation device 50 verifies whether safety is secured for the patient 72 when the received motion request is executed with the slave device 30 (SQ32 in FIG. 7). In this operation, suppose that the motion request is received after the time t2.

As illustrated in FIG. 9, the motion request by the surgeon 71 has been issued on the basis of the virtual slave environment 710t1 at the time t1, but the virtual slave environment has been updated to the virtual slave environment 710t2 until the simulation device 50 receives the motion request 150. For this reason, in the present embodiment, the simulation device 50 executes processing to verify the safety using the virtual slave environment 710t2, not the virtual slave environment 710t1. In the processing to verify the safety, it is possible to use a virtual slave environment 710ti (i is a natural number of 2 or more) reconstructed until the point in time when the motion request 150 is received after reconstruction of the virtual slave environment 710t1. However, it is desired to use the latest virtual slave environment (virtual slave environment 710t2 in this case) at the point in time when the motion request 150 is received.

For example, the following is consideration of the case where the simulation device 50 executes simulation using the virtual slave environment 710t1 used with the master device 20 when the motion request 150 is transmitted, without using the latest virtual slave environment 710t2 at the point in time when the motion request 150 is received.

Suppose that the shape of the lesion 721 of the patient 72 has been rapidly changed between the time t1 to the time t2. In this case, when simulation is executed for the motion request using the virtual slave environment 710t1 of the time t1, the simulation device 50 determines that no problem for safety exists. However, as described above, due to the rapid change in shape of the lesion 721 at the time t2, when the motion request 150 is actually executed, the motion execution unit 35 contacts the lesion 721 with the rapidly changed shape. Specifically, the motion execution unit 35 unintendedly contacts part of the lesion, and safety is lost with high possibility.

By contrast, when simulation is executed for the motion request 150 using the latest virtual slave environment 710t2 at the point in time when the motion request 150 is received, the rapid change in shape of the lesion 721 has already been reflected in the virtual slave environment 710t2. In addition, the simulation produces the result in which motion execution unit 35 invades the lesion 721 having the rapidly changed shape when the motion request 150 for the motion execution unit 35 is executed. Specifically, the simulation device 50 determines that no safety is secured. This structure enables the simulation device 50 to take action of transition to the safe state before executing the motion request 150 for the patient 72, without executing verification for the master device 20.

Although this example illustrates a rapid change in shape of the lesion 721 as an example, it is also possible to take action of transition to the safe state before execution of the motion request for the patient 72, in the case where the motion execution unit 35 of the slave device 30 does not move within the preset range of position, velocity, and/or acceleration, the case where the motion execution unit 35 does not contact the lesion 721 within the preset force range, and/or the case where communication between the simulation device 50 and the master device 20 is disconnected.

With reference to FIG. 7 again, when safety is verified at SQ32, the simulation device 50 transmits the motion request with the verified safety to the slave device 30 (SQ33 in FIG. 7). Thereafter, the slave device 30 executes the motion request (SQ34 in FIG. 7). The processing described above is the processing of verifying safety in the case where the virtual slave environment serving as the basis at the time when the master device 20 transmits the motion request is different from the latest virtual slave environment at the time when the simulation device 50 receives the motion request. Although it is not illustrated, in the case where safety is not verified at SQ32, the simulation device 50 transmits a motion switch instruction to the slave device 30, and processing of transition to the safe state is executed.

Figure 10A:
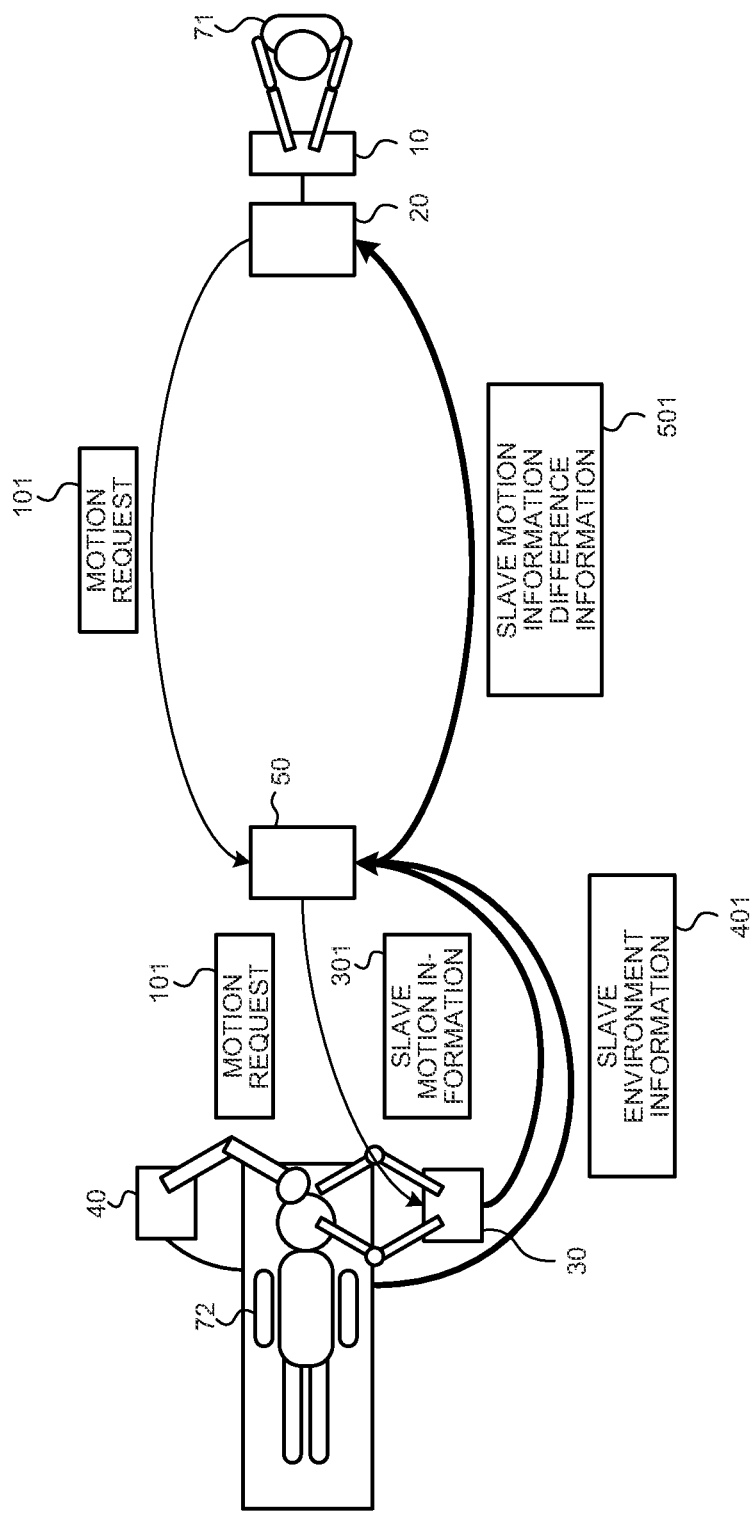
FIG. 10A is a diagram schematically illustrating an example of flow of information in the remote operation system according to the embodiment.

FIGS. 10A, 10B, and 10C are diagrams schematically illustrating an example of flow of information in the remote operation system according to the embodiment. In the motion stop sensing processing or the motion request verification processing, when transition to the safe state is not executed, information is transmitted and received between the slave environment observation device 40, the slave device 30, the simulation device 50, and the master device 20, as illustrated in FIG. 10A. Specifically, the slave environment observation device 40 transmits slave environment information 401 to the simulation device 50, and the slave device 30 transmits slave motion information 301 to the simulation device 50. The simulation device 50 transmits difference information and slave motion information 501 to the master device 20. By contrast, the master device 20 transmits a motion request 101 other than an emergency stop request to the simulation device 50. The simulation device 50 transmits the motion request 101 with verified safety to the slave device 30.

By contrast, as illustrated in FIG. 10B, when communication with the master device 20 is disconnected or change in state caused by delay in communication, the simulation device 50 transmits a safe state transition instruction to the slave device 30.

In addition, as illustrated in FIG. 10C, when an emergency stop request 102 is issued, the master device 20 directly transmits the emergency stop request 102 to the slave device 30 without going through the simulation device 50. This is because the processing can be safely stopped without verifying safety with the simulation device 50, with respect to stop of the motion of the motion execution unit of the slave device 30.

The explanation described above illustrates a remote medical system in which the surgeon 71 executes treatment remotely for the patient 72, as an example of the remote operation system 1. However, the present embodiment is not limited thereto, but is useful for application for which safety is to be secured. Examples thereof include executing nursing and care from a remote place with a service robot, and operating a mobile robot from a remote place. More specifically, the present embodiment is also applicable to infrastructure inspection or work in a place where no person can work, such as bridges and nuclear power plants, work of remote rubble removal for rescue in a disaster, and/or work in a mining place or a construction site. The present embodiment is also applicable to scenes in which complete automation is difficult and an operation by human from a remote place is required, for example, work support in a store, such as display, cleaning, and guard, and life support, such as cooking and washing. The slave device 30 may have any form suitable for the use thereof, such as an arm type, a wheel-traveling type, and a flying (drone) type.

In the embodiment, the simulation device 50 receives a motion request for the slave device 30, and the motion request is generated with the master device 20 on the basis of the first slave environment information for the treatment target and the first slave motion information for the motion execution unit of the slave device 30. The simulation device 50 is configured to issue a motion request on the basis of the second slave environment information and the second slave motion information updated during the time after reception of the first slave environment information and the first slave motion information and before reception of the motion request. This structure enables sensing of abnormality of the treatment target or the slave device 30 generated after reception of the first slave environment information and the first slave motion information serving as the basis of the motion request. This structure enables instruction of transition to the safe state without issuing a motion request, when securement of safety for the treatment target in execution of the motion request is difficult due to the abnormality. Specifically, because only the motion request with the verified safety is executed, the simulation device 50 is enabled to avoid risk that cannot be sensed with the master device 20 side due to communication delay or the like. This structure also enables autonomous securement of safety between the simulation device 50 and the slave device 30.

This structure secures stability of control and safety of the work environment, even in an environment in which time delay until the motion request from the master device 20 reaches the slave device 30 occurs and time delay occurs when change in environment of the slave device 30 side is fed back to the master device 20 side. In particular, this structure enables avoidance of careless damage to the patient while executing a minute surgical tool operation by treatment from a remote place in a surgical treatment. In addition, this structure enables sensing of risk between the slave device 30 and the simulation device 50 and transition to the safe state, even when the communication state between the physically distant master device 20 and the slave device 30 is unstable.

In addition, the simulation device 50 reconstructs the virtual slave environment on the basis of the slave environment information and the slave motion information, and simulates the motion request in the virtual slave environment. This structure enables prediction of a phenomenon occurring with the motion request with high accuracy.

In addition, the master device 20 directly transmits some requests, such as an emergency stop request, to the slave device 30 without relaying the simulation device 50. With this structure, no simulation is executed for the emergency stop request in the simulation device 50. This structure enables more prompt transmission of a risk avoiding operation from the master device 20 side to the slave device 30.

In addition, the master device 20 reconstructs the virtual slave environment of virtual reality using the slave environment information and the slave motion information. This structure enables presentation of a free viewpoint image enabling easy operation to the master device 20. In addition, because the slave environment model modeled in advance is shared between the master device 20 and the simulation device 50, it suffices that the simulation device 50 transmits difference information between the reconstructed virtual slave environment and the previously reconstructed virtual slave environment to the master device 20 side. This structure enables reduction in communication data during execution.

The slave device 30 of the remote operation system 1 described above may have the structure in which a motion request execution unit 32 is provided on the motion execution unit, or the structure in which a motion request execution unit 32 is provided for a plurality of motion execution units. Specifically, the remote operation system 1 may be provided with a plurality of slave device 30 in each of which the motion execution unit and the motion request execution unit 32 are associated with each other one to one, or a slave device 30 in which a plurality of motion execution units are associated with a motion request execution unit 32. The explanation described above illustrates the case where a simulation device 50 is provided in the remote operation system 1, but a plurality of simulation devices 50 may be provided.

Hardware Configuration

Figure 11:
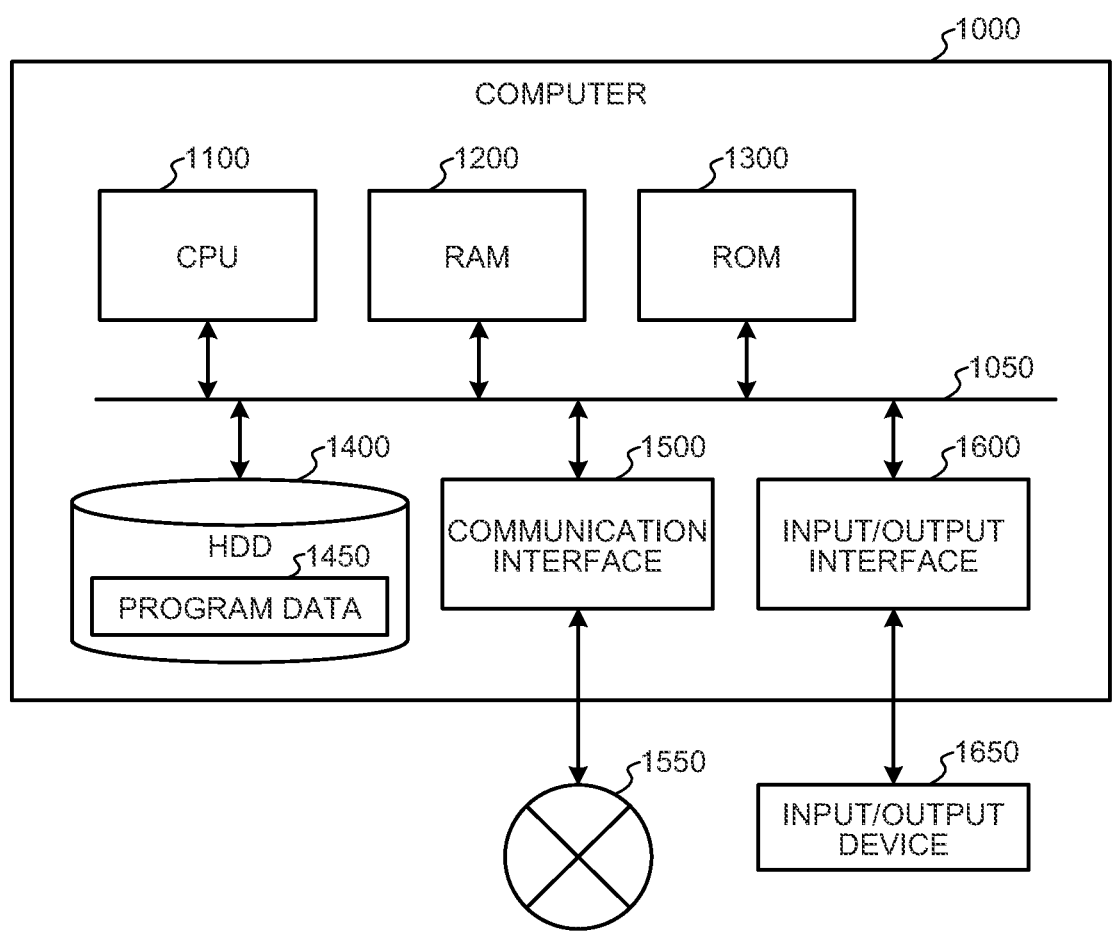
FIG. 11 is a hardware configuration diagram illustrating an example of a computer achieving functions of the information processing apparatus according to the embodiment.

FIG. 11 is a hardware configuration diagram illustrating an example of a computer achieving functions of the information processing apparatus according to the embodiment. The information processing apparatus in the embodiment described above, such as the master device 20 and the simulation device 50, is achieved with a computer 1000. The computer 1000 includes a CPU 1100, a RAM 1200, a read only memory (ROM) 1300, a hard disk drive (HDD) 1400, a communication interface 1500, and an input/output interface 1600. The units of the computer 1000 are connected via a bus 1050.

The CPU 1100 operates on the basis of computer programs stored in the ROM 1300 or the HDD 1400, and controls each of the units. For example, the CPU 1100 develops the computer programs stored in the ROM 1300 or the HDD 1400 to the RAM 1200, and executes processing corresponding to the respective computer programs.

The ROM 1300 stores therein a boot program, such as a basic input output system (BIOS) executed with the CPU 1100 when the computer 1000 is started up, and a computer program depending on the hardware of the computer 1000, and the like.

The HDD 1400 is a computer-readable recording medium non-temporally recording a computer program executed with the CPU 1100 and data used with the computer program, and the like. Specifically, the HDD 1400 is a recording medium recording the information processing program according to the present disclosure being an example of program data 1450.

The communication interface 1500 is an interface to connect the computer 1000 with an external network 1550 (for example, the Internet). For example, the CPU 1100 receives data from another apparatus and transmits data generated with the CPU 1100 to another apparatus, via the communication interface 1500.

The input/output interface 1600 is an interface to connect an input/output device 1650 with the computer 1000. For example, the CPU 1100 receives data from an input device, such as a keyboard and a mouse, via the input/output interface 1600. In addition, the CPU 1100 transmits data to an output device, such as a display, a speaker, and a printer, via the input/output interface 1600. The input/output interface 1600 may also function as a medium interface reading a computer program or the like recorded on a certain recording medium (medium). The medium is an optical recording medium, such as a digital versatile disc (DVD) and a phase change rewritable disk (PD), a magneto-optical recording medium, such as a magneto-optical disk (MO), a tape medium, a magnetic recording medium, or a semiconductor memory or the like.

For example, when the computer 1000 functions as the simulation device 50 according to the embodiment, the CPU 1100 of the computer 1000 achieves functions of the virtual slave environment reconstruction unit 54, the difference information extraction unit 55, the motion stop sensing unit 56, the motion request verifying unit 57, and the safe state transition unit 58, by executing the information processing program loaded onto the RAM 1200. In addition, the HDD 1400 stores therein the information processing program according to the present disclosure and the data in the slave environment model storage unit 53. The CPU 1100 reads the program data 1450 from the HDD 1400 and executes the program data 1450, but these computer programs may be acquired from another device via the external network 1550, as another example.

The effects described in the present specification are mere examples and not limited thereto, but the structure may include other effects.

The present technique may also have the following structures.

(1)

An information processing apparatus comprising a motion request verifying unit controlling execution of a motion request for a device on the basis of the motion request based on device side information including device state information indicating a state of the device at a first point in time and target state information indicating a state of an operated target, and device side information updated during time after the first point in time and before a second point in time at which the motion request is received.

(2)

The information processing apparatus according to (1), further comprising:
 a virtual target environment reconstruction unit reconstructing a virtual target environment using an environment model for the target, the updated target state information, and the updated device state information, wherein
 the motion request verifying unit controls execution of the motion request on the basis of a simulation result for the motion request in the virtual target environment.

(3)

The information processing apparatus according to (2), wherein the motion request verifying unit does not execute the motion request when the simulation result for the motion request hinders safety of the target.

(4)

The information processing apparatus according to any one of (1) to (3), further comprising a motion stop sensing unit sensing whether to stop a motion of the device on the basis of the updated device side information.

(5)

The information processing apparatus according to (2), further comprising a motion stop sensing unit sensing whether to stop a motion of the device on the basis of a relation between the device and the target in the virtual target environment.

(6)

The information processing apparatus according to any one of (1) to (5), wherein an update cycle of the device side information is shorter than a reception interval of the motion request.

(7)

The information processing apparatus according to any one of (1) to (6), wherein
 the target is a patient,
 the device is a motion execution unit executing treatment for the patient,
 the device state information indicates a position and a motion state of the motion execution unit, and
 the target state information is a state of a lesion and biological information of the patient.

(8)

An information processing method comprising controlling execution of a motion request for a device on the basis of the motion request based on device side information including device state information indicating a state of the device at a first point in time and target state information indicating a state of an operated target, and device side information updated during time after the first point in time and before a second point in time at which the motion request is received.

(9)

A computer program to achieve a function of controlling execution of a motion request for a device on the basis of the motion request based on device side information including device state information indicating a state of the device at a first point in time and target state information indicating a state of an operated target, and device side information updated during time after the first point in time and before a second point in time at which the motion request is received.

REFERENCE SIGNS LIST

1 REMOTE OPERATION SYSTEM
10 MASTER CONSOLE
11 INFORMATION PRESENTATION UNIT
12 OPERATION INPUT UNIT
20 MASTER DEVICE
21, 31, 42 COMMUNICATION UNIT
22, 53 SLAVE ENVIRONMENT MODEL STORAGE UNIT
23, 54 VIRTUAL SLAVE ENVIRONMENT RECONSTRUCTION UNIT
30 SLAVE DEVICE
32 MOTION REQUEST EXECUTION UNIT
35 MOTION EXECUTION UNIT
40 SLAVE ENVIRONMENT OBSERVATION DEVICE
41 ENVIRONMENT OBSERVATION UNIT
50 SIMULATION DEVICE
51 MASTER COMMUNICATION UNIT
52 SLAVE COMMUNICATION UNIT
55 DIFFERENCE INFORMATION EXTRACTION UNIT
56 MOTION STOP SENSING UNIT
57 MOTION REQUEST VERIFICATION UNIT
58 SAFE STATE TRANSITION UNIT

The invention claimed is:

1. An information processing apparatus, comprising:
 a motion request verifying unit configured to:
  control execution of a motion request for a slave device based on the motion request, wherein
   the motion request is based on device side information that includes slave device state information indicating a state of the slave device at a first point in time,
  update the device side information during a time after the first point in time and before a second point in time, wherein
   the second point in time is a time at which the motion request is received, and
  update the slave device state information based on the updated device side information; and
 a virtual slave environment reconstruction unit configured to reconstruct virtual slave environment based on environment information and the updated slave device state information, wherein
  the motion request verifying unit is further configured to control the execution of the motion request for the slave device based on a result of a simulation in the virtual slave environment.

2. The information processing apparatus according to claim 1, further comprising:
 a virtual target environment reconstruction unit configured to reconstruct a virtual target environment based on an environment model for a target, updated target state information, and the updated slave device state information, wherein
  the motion request verifying unit is further configured to control execution of the motion request based on a simulation result for the motion request in the virtual target environment.

3. The information processing apparatus according to claim 2, wherein the motion request verifying unit does not execute the motion request based on determination that the simulation result for the motion request hinders safety of the target.

4. The information processing apparatus according to claim 1, further comprising a motion stop sensing unit configured to sense whether to stop a motion of the slave device based on the updated device side information.

5. The information processing apparatus according to claim 2, further comprising a motion stop sensing unit configured to sense whether to stop a motion of the slave device based on a relation between the slave device and the target in the virtual target environment.

6. The information processing apparatus according to claim 1, wherein an update cycle of the device side information is shorter than a reception interval of the motion request.

7. The information processing apparatus according to claim 1, wherein
the device side information further includes target state information indicating a state of a target,
the target is a patient,
the slave device is a motion execution unit configured to execute treatment for the patient,
the slave device state information indicates a position and a motion state of the motion execution unit, and
the target state information includes a state of a lesion and biological information of the patient.

8. An information processing method, comprising:
controlling execution of a motion request for a slave device based on the motion request, wherein
the motion request is based on device side information that includes slave device state information indicating a state of the slave device at a first point in time;
updating the device side information during time after the first point in time and before a second point in time, wherein
the second point in time is a time at which the motion request is received;
updating the slave device state information based on the updated device side information;
reconstructing virtual slave environment based on environment information and the updated slave device state information; and
controlling the execution of the motion request for the slave device based on a result of a simulation in the virtual slave environment.

9. A non-transitory computer-readable medium having stored thereon, computer-executable instructions which, when executed by a computer, cause the computer to execute operations, the operations comprising:
controlling execution of a motion request for a slave device based on the motion request, wherein
the motion request is based on device side information that includes slave device state information indicating a state of the slave device at a first point in time;
updating the device side information during time after the first point in time and before a second point in time, wherein
the second point in time is a time at which the motion request is received;
updating the slave device state information based on the updated device side information;
reconstructing virtual slave environment based on environment information and the updated slave device state information; and
controlling the execution of the motion request for the slave device based on a result of a simulation in the virtual slave environment.

* * * * *